(12) United States Patent
Bickel et al.

(10) Patent No.: US 6,691,867 B1
(45) Date of Patent: Feb. 17, 2004

(54) SHARPS DISPOSAL ASSEMBLY HAVING USER-FRIENDLY UNWINDING FEATURE

(76) Inventors: Christopher R. Bickel, 52 Jacksonville Dr., Parsippany, NJ (US) 07054; Gregory P. Reimer, 12 Tysley St., Basking Ridge, NJ (US) 07920; John D. Macarell, Jr., 10 Longview Rd., High Crest Lake, West Milford, NJ (US) 07480

( * ) Notice: Subject to any disclaimer, the term of this patent is extended or adjusted under 35 U.S.C. 154(b) by 0 days.

(21) Appl. No.: 09/559,041

(22) Filed: Apr. 27, 2000

(51) Int. Cl.[7] ............................................... B65D 83/10
(52) U.S. Cl. ....................................... 206/366; 206/370
(58) Field of Search ............................... 206/363–366, 206/370; 220/908; 604/110

(56) References Cited

U.S. PATENT DOCUMENTS

| | | |
|---|---|---|
| 4,375,849 A | 3/1983 | Hanifl |
| 4,466,538 A | 8/1984 | Gianni |
| 4,657,139 A | 4/1987 | Hanifl |
| D292,037 S | 9/1987 | Hanifl |
| 4,779,728 A | 10/1988 | Hanifl et al. |
| 4,842,138 A | 6/1989 | Sandel et al. |
| 4,863,057 A | 9/1989 | Hanifl et al. |
| D304,109 S | 10/1989 | Hanifl |
| RE33,143 E | 1/1990 | Grone |
| 4,892,191 A * | 1/1990 | Nakamura .................. 206/366 |
| D306,509 S | 3/1990 | Hanifl et al. |
| D307,841 S | 5/1990 | Hanifl et al. |
| 4,984,686 A | 1/1991 | Shillington |
| 5,092,462 A | 3/1992 | Sagstetter et al. |
| 5,107,990 A | 4/1992 | Wickerski et al. |
| 5,273,161 A * | 12/1993 | Sagstetter .................. 206/366 |
| 5,322,164 A * | 6/1994 | Richardson et al. ........ 206/366 |
| 5,346,086 A | 9/1994 | Harris |
| 5,402,887 A * | 4/1995 | Shillington ................. 206/366 |
| 5,415,315 A | 5/1995 | Ramirez |

* cited by examiner

Primary Examiner—Luan K. Bui
(74) Attorney, Agent, or Firm—Richard E. Brown; Scott J. Rittman, Esq.

(57) ABSTRACT

A sharps disposal assembly has a recessed unwinder opening in a container lid. The recess has a vertical wall portion integral with a horizontal platform for locating the bottom wall of a tube holder. Another vertical wall portion depending downwardly from the platform has a width congruent with the nose portion of the tube holder.

3 Claims, 6 Drawing Sheets

SHARPS DISPOSAL ASSEMBLY HAVING USER-FRIENDLY UNWINDING FEATURE

FIELD OF THE INVENTION

This invention relates to medical devices and more particularly relates to blood sampling devices and safe disposal thereof.

BACKGROUND OF THE INVENTION

Many medical articles used in hospitals and clinics are designed for one-time use. Articles which have sharp points, cutting edges and like, are collectively known as sharps, and many disclosures of special equipment and procedures have been proposed to minimize the danger of injury, such as needle stick, to personnel involved in the use of these articles. Safe handling and disposal is particularly important, since a sharp is often used in a procedure, such as blood sampling, and as a result may be contaminated with a potentially infectious agent.

Many designs of disposal equipment for sharps have been proposed. Most include a storage container having a lid with locking closure features and several openings through the lid for access to the interior of the container. Often the sharp is affixed to a hub having threads mated to a tube holder, and it is conventional that one of the openings have structure associated therewith, known as the unwinder, for unthreading the sharp from the holder without any manual manipulation by the user.

Conventional unwinders operate by inserting a needle-hub unit into the large end of a V-shaped opening and advancing the unit toward the narrow end of the opening until ribs on the hub engage the wall of the unwinder. At this point, a twisting rotation of the needle holder causes the hub and needle drop off into the container. Typical sharps disposal containers having an unwinder designed to unthread needles from a hub are disclosed in U.S. Pat. No. 4,375,849 to Hanifl, U.S. Pat. No. 5,415,315 to Ramiriz et al, and U.S. Pat. No. 4,466,538 to Gianni. An unwinder for double-ended needles is disclosed in U.S. Pat. No. 5,092,462 to Sagstetter et al.

Reports from field use of prior art sharps disposal equipment have repeatedly pointed to difficulties encountered in engaging the ribs of a needle-hub unit with the unwinder. With prior art assemblies, the practictioner has only visual guidance and trial and error for positioning the unit, otherwise the ribs are askew relative to the unwinder and engagement cannot occur. This deficiency may lead to accidents, such as tipping of the assembly and inadvertent needle stick of technician or subject. There is a need in the art for sharps disposal equipment which overcomes this prior art deficiency. The present invention addresses this need.

SUMMARY OF THE INVENTION

A sharps disposal assembly has a container and a cap therefor. A plate section of the cap defines a recessed unwinder opening therethrough. A first vertical wall depends downwardly from the plate and circumscribes a recessed platform portion of the unwinder for receiving the bottom wall of a tube holder. A second vertical wall portion depends downwardly from the platform, has a width which is congruent with the width of the nose portion of the tube holder and circumscribes a horizontal shelf portion of the unwinder. A third vertical wall portion of the unwinder depends downwardly from the shelf and may optionally include one or more vertical shoulders projecting therefrom to engage a rib on a needle hub to be unwound.

Thus, when a needle hub unit is to be unwound for disposal, the bottom wall of the tube holder is easily positioned properly by visual and tactile recognition of the recessed platform. The congruity of the length of the nose portion of the holder and the width of the first vertical wall portion assures perfect vertical alignment of the needle-hub unit so that easy, error-free advancement and engagement with the unwinder can be carried out, with no trial and error, using tactile guidance only.

Thus, all the guesswork and trial and error for proper positioning inherent in use of prior art assemblies is eliminated with the assembly of the invention.

DETAILED DESCRIPTION

While this invention is satisfied by embodiments in many different forms, there will herein be described in detail a preferred embodiment of the invention with the understanding that the present disclosure is to be considered as exemplary of the principles of the invention and is not intended to limit the invention to the embodiments illustrated and described. The scope of the invention will be measured by the appended claims and their equivalents.

The following description is directed to the embodiment of the invention wherein the assembly is used to unwind a needle-hub unit threaded to a needle holder with the understanding that the principles of the invention may be used to unwind threaded components of any medical article to be discarded.

Figure 1:
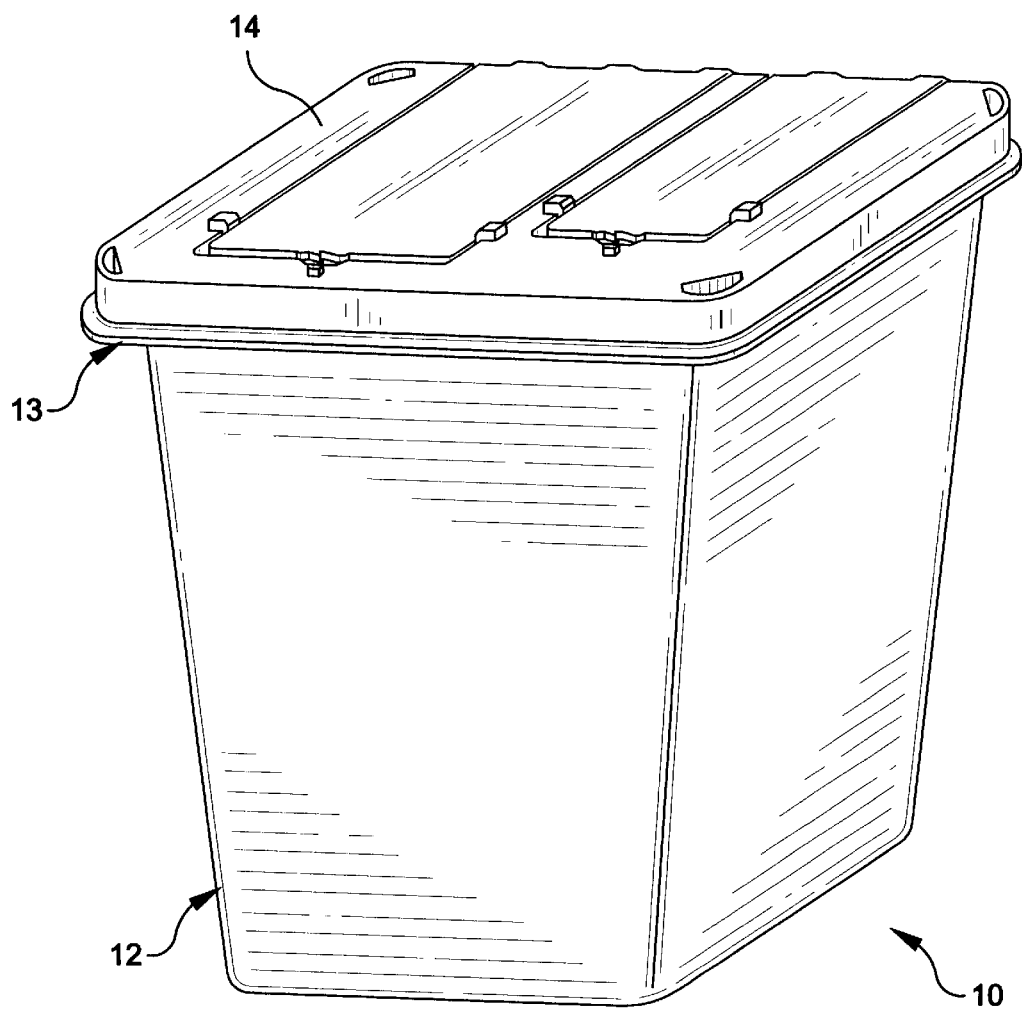
FIG. 1 is a perspective view of the sharps disposal assembly of the invention with the flaps closed.
Figure 2:
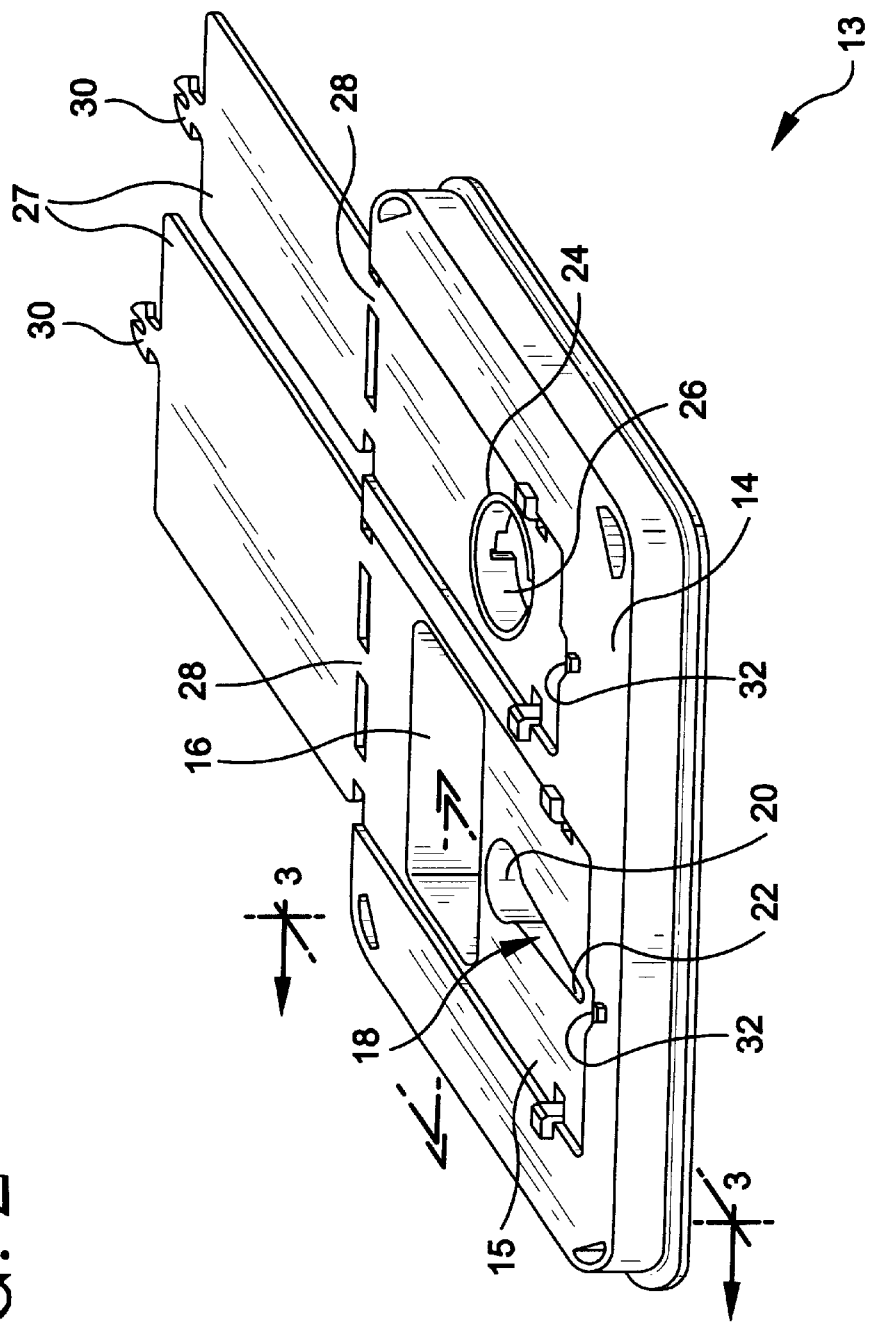
FIG. 2 is a perspective view of the cap of the assembly of FIG. 1 with the flaps open.

Adverting now to the drawings, wherein like elements are given the same reference number followed by a lower case letter in the various illustrations thereof, FIGS. 1 and 2 illustrate a sharps disposal assembly 10 including a receptacle 12 and a cap 13. Cap 13 has a substantially flat top surface 14 which includes a plate section 15. Plate section 15 has a large port opening 16 and an unwinder opening 18, preferably V shaped, therethrough. Port opening 16 may be of any suitable geometrical configuration, but for the purpose of illustration, is shown in the preferred rectangular shape. Alternatively, the port and unwinder openings may be combined into a single, continuous opening. Unwinder opening 18 is recessed below the level of plate 15 and extends from a large end 20 to a narrow end 22.

Cap 13 also has a circular opening 24 with insert 26 therein expressly dimensioned to engage a SAFETY-GARD™ tube holder, as sold by Becton, Dickinson and Company. Opening 24 and insert 26 are conventional features of prior art sharps disposal receptacles and are fully described in the aforementioned U.S. Pat. No. 5,092,462.

Flaps 27 are affixed to cap 13 by integral tabs 28 and have integral closure tabs 30 dimensioned for insertion into slots 32 in cap 13 to cover the openings.

Figure 4:
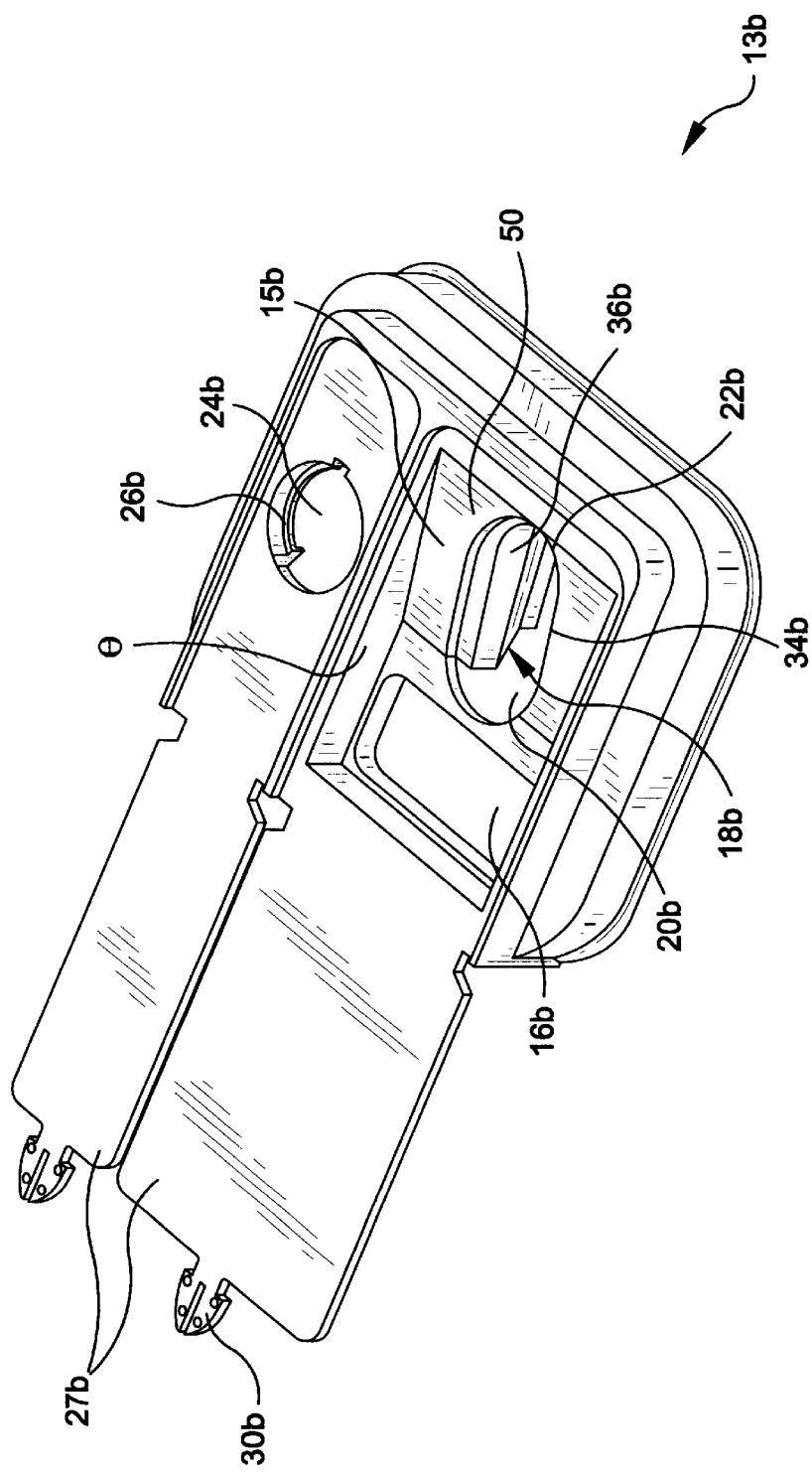
FIG. 4 is a side angle perspective view of the cap portion of a preferred assembly.

Plate section 15 of cap 13 may preferably be slanted at an angle theta to the plane of top surface 14 of cap 13. This optional feature is illustrated in FIG. 4 directed to the preferred embodiment of the assembly. Angle theta may be from 5–20°, preferably 10–15°.

Figure 3:
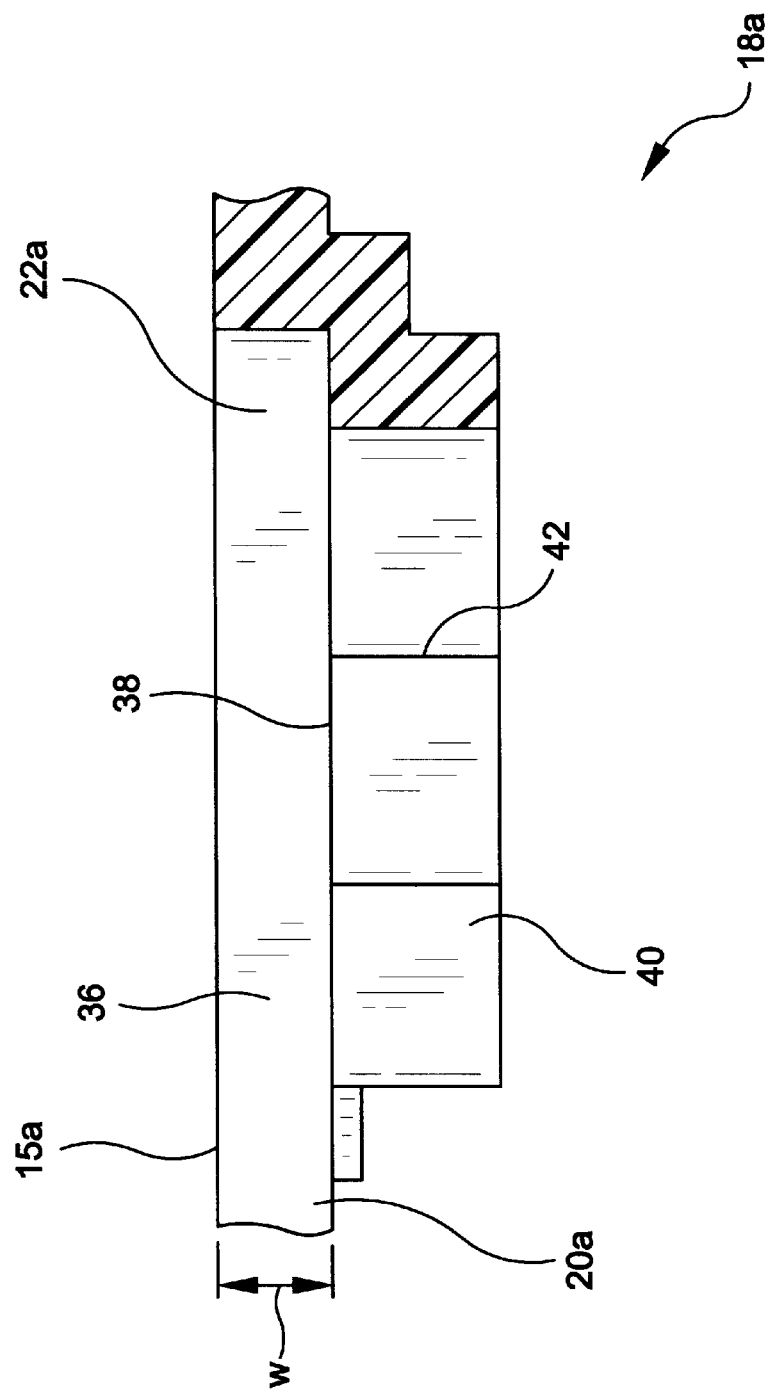
FIG. 3 is a horizontal sectional view of the cap of FIG. 2 taken along the line 3—3 thereof showing details of the unwinder section.
Figure 7:
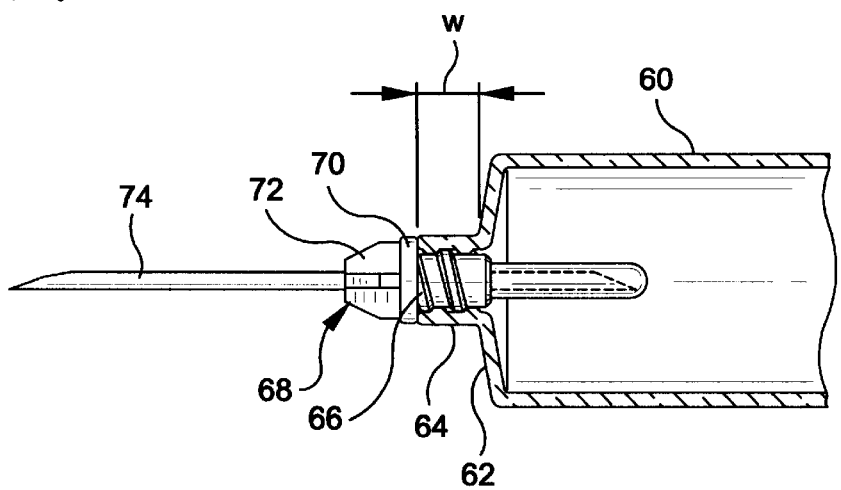
FIG. 7 is a perspective view of a typical needle holder assembly as known in the art.

As shown in FIG. 3, a wall portion 36 of unwinder 18a is vertically disposed downward from plate 15a. Wall portion 36 is of particular width w which matches the length of the nose portion of a conventional tube holder, as shown in FIG. 7. Wall portion 36 is integral with a horizontal unwinder shelf portion 38 which in turn is integral with a vertical wall portion 40. Wall portion 40 may optionally have one or more vertical shoulders 42 projecting outwardly therefrom.

Figure 5:
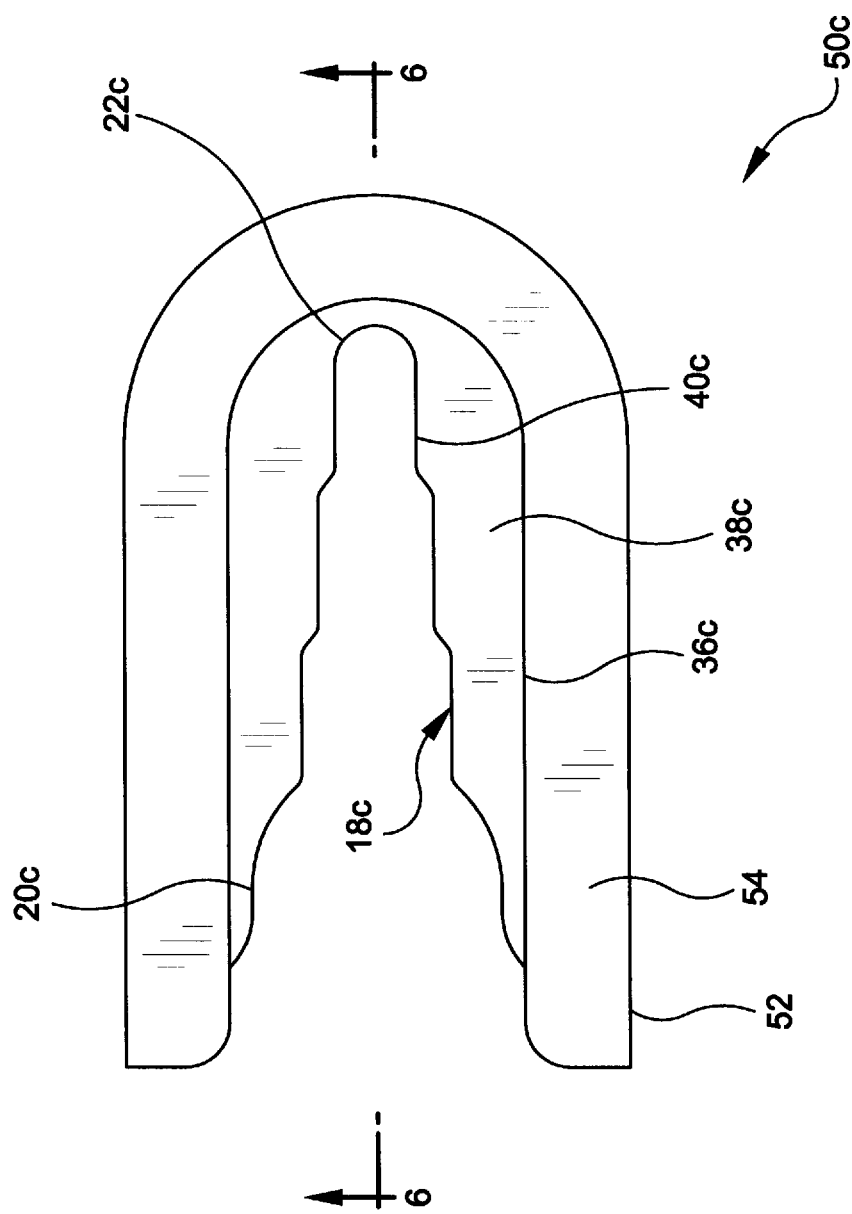
FIG. 5 is an enlarged top perspective view of the unwinder section of the cap of FIG. 4.
Figure 6:
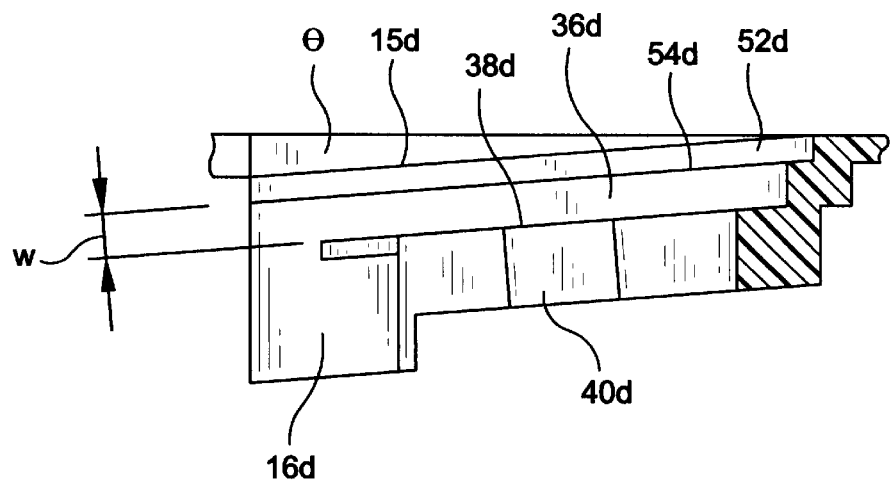
FIG. 6 is a horizontal sectional view of the unwinder section of FIG. 5 taken along the line 6—6 thereof.

A preferred embodiment of the sharps disposal assembly is illustrated in FIGS. 4–6. Plate 15b is slanted at an angle theta relative to the plane of the top surface of cap 13b whereby the narrow end 22b of the unwinder is higher than the wide end 20b.

Unwinder 18b is part of a recess 50 through plate 15b. A first segment of recess 50 is a wall 52 vertically disposed downwardly from the plate. Wall 52 circumscribes a horizontal platform 54 connected to a second vertical wall portion 36c of width w. The second wall portion circumscribes a horizontal shelf portion 38c which is connected to a third vertical wall portion 40c. Wall portion 40c may optionally have one or more shoulders (not shown in FIGS. 4–6) projecting vertically therefrom.

For purposes of illustration of the sharps disposal assembly of the invention, FIG. 7 identifies key components of a conventional needle holder assembled to a needle hub unit. Needle holder 60 has flat bottom portion 62 and nose portion 64 having internal threads 66 for engaging mating threads on a needle-hub unit. The needle-hub unit includes hub 68 having top flange 70, ribs 72 and needle 74. The distance from bottom portion 62 of holder 60 to the end of nose portion 64 is indicated as w.

In use of the preferred assembly of the invention, the technician, grasping needle holder 60, inserts nose portion 64 with the attached needle-hub unit through the large end 20 of the unwinder opening 18 using platform 54 as an easy, error-proof visual and tactile guide for positioning bottom portion 62 of holder 60 onto the platform. With this configuration, the needle-hub unit assumes the ideal perpendicular orientation to shelf 38 for advancement, regardless of whether or not the assembly in use includes slope 15. With the holder thus positioned, it is advanced into the unwinder, using tactile guidance only, the congruity of distance w for both the holder assembly and vertical wall portion 36 of the unwinder providing perfect engagement of the ribs 70 of hub 68 with unwinder wall portion 40, or with a shoulder 42 thereon. All guesswork and trial and error are eliminated resulting in error-free unwinding.

The assembly of the invention may be made of any suitable plastic, such as polyethylene, polypropylene and polyvinyl chloride. The lid with the unwinder elements is preferably made by conventional injection molding with integral construction wherein all the parts are continuous with no seams therebetween.

What is claimed:

1. A sharps disposal assembly comprising:
    a) a substantially rigid storage receptacle;
    b) a cap for said receptacle having a flat top surface and a plate section, said plate section being slanted downwardly at an angle from the plane of said top surface and defining a plurality of openings into said receptacle, a first of said openings being a V-shaped unwinder opening;
    c) a recess in said plate including said unwinder opening, said recess being bounded by a first vertical wall projecting downwardly from said plate section and circumscribing a horizontal platform, said platform connecting to a second vertical wall projecting downwardly from said platform and circumscribing a horizontal shelf, said shelf connecting to a third vertical wall, said second wall having a width matching the length of a nose portion of a tube holder; and
    d) flaps affixed to said cap to cover said openings.

2. The assembly of claim 1 wherein a second of said openings is substantially rectangular and dimensioned to receive a large medical article.

3. The assembly of claim 2 wherein said flat top surface defines a third annular opening containing an insert to engage a needle holder.

* * * * *